US007955601B2

(12) United States Patent
Elvin et al.

(10) Patent No.: US 7,955,601 B2
(45) Date of Patent: Jun. 7, 2011

(54) **IMMUNOGENIC AGENTS AGAINST *BURKHOLDERIA PSUDOMALLEI* AND/OR *BURKHOLDERIA MALLEI*, COMPRISING LIPOPOLYSACCHARIDE, CAPSULAR POLYSACCHARIDE AND/OR PROTEINS FROM *BURKHOLDERIA PSEUDOMALLEI***

(75) Inventors: Stephen John Elvin, Salisbury (GB); Gareth David Healey, Salisbury (GB); Ethel Diane Williamson, Salisbury (GB); James Edward Eyles, Salisbury (GB); Sophie Jane Smither, Salisbury (GB); Mitali Sarkar-Tyson, Salisbury (GB); Timothy Philip Atkins, Salisbury (GB); Michelle Nelson, Salisbury (GB); Richard William Titball, Salisbury (GB)

(73) Assignee: The Secretary of State for Defence, Salisbury, Wiltshire (GB)

( * ) Notice: Subject to any disclaimer, the term of this patent is extended or adjusted under 35 U.S.C. 154(b) by 141 days.

(21) Appl. No.: 12/088,748

(22) PCT Filed: Oct. 2, 2006

(86) PCT No.: PCT/GB2006/003628
§ 371 (c)(1),
(2), (4) Date: Oct. 28, 2008

(87) PCT Pub. No.: WO2007/036735
PCT Pub. Date: Apr. 5, 2007

(65) Prior Publication Data
US 2009/0220548 A1    Sep. 3, 2009

(30) Foreign Application Priority Data
Sep. 30, 2005   (GB) .................... 0519871.8

(51) Int. Cl.
*A61K 39/00*     (2006.01)
*A61K 39/02*     (2006.01)
(52) U.S. Cl. .................... 424/184.1; 424/234.1
(58) Field of Classification Search .................. None
See application file for complete search history.

(56) References Cited

U.S. PATENT DOCUMENTS

| | | | |
|---|---|---|---|
| 4,879,213 A * | 11/1989 | Fox et al. ................ | 435/5 |
| 5,338,543 A | 8/1994 | Fitzgerald et al. | |
| 5,565,205 A | 10/1996 | Petersen et al. | |
| 6,429,199 B1 | 8/2002 | Krieg et al. | |
| 2010/0055123 A1 | 3/2010 | Harland | |
| 2010/0062022 A1 | 3/2010 | Harding et al. | |

FOREIGN PATENT DOCUMENTS

| | | |
|---|---|---|
| EP | 0 761 819 | 3/1997 |
| GB | 2345061 A | 6/2000 |
| WO | WO-9710351 | 3/1997 |
| WO | WO 00/56282 | 9/2000 |
| WO | WO 00/56361 | 9/2000 |
| WO | WO 00/56362 | 9/2000 |
| WO | WO 01/55398 | 8/2001 |
| WO | WO 03/073351 | 9/2003 |
| WO | WO 2004/006857 | 1/2004 |
| WO | WO 2006/109071 | 10/2006 |
| WO | WO 2006/109071 A2 | 10/2006 |

OTHER PUBLICATIONS

Plotkin et al (Vaccines, W. B. Saunders Co. 1988, p. 571).*
Cooper et al (Vaccine vol. 22, pp. 3136-3143, 2004).*
Garmory, et al., 'ATP-Binding Cassette Transporters Are Targets for the Development of Antibacterial Vaccines and Therapies,' *Infection and Immunity*, 72(12):6757-6763 (2004) XP-002399895.
Higgins, et al., 'ABC Transporters: From Microorganisms to Man,' *Annu. Rev. Cell Biol.*, 8:67-113 (1992).
Holden, et al., Genomic plasticity of the causative agent of melioidosis, *Burkholderia pseudomallei*, *Proc. Natl. Acad. Sci.*, 101(39):14240-14245 (2004).
Database EMBL Sep. 16, 2004 '*Burkholderia pseudomallei* strain K96243, chromosome 1, complete sequence,' XP002399907 retrieved from EBI accession No. EM_PRO:BX571965 Database accession No. BX571965.
Database EMBL Sep. 16, 2004 '*Burkholderia pseudomallei* strain K96243, chromosome 2, complete sequence' XP002399908 retrieved from EBI accession No. EM_PRO:BX571966 Database accession No. BX571966 abstract.
Database UniProt Oct. 25, 2004 'Putative lipoprotein releasing system transmembrane protein' XP002399909 retrieved from EBI accession No. UNIPROT;Q63SP3_BURPS Database accession No. Q63SP3 abstract.
Database UniProt Oct. 25, 2004 'Putrescine-bindinng periplasmic protein' XP002399910 retrieved from EBI accession No. UNIPROT;Q63UP1_BURPS Database accession No. Q63UP1 abstract.
Database UniProt Oct. 25, 2004 'Pitative periplasmic oligopeptide-binding protein' XP002399911 retrieved from EBI accession No. UNIPROT:Q63IDO_BURPS Database accession No. Q63IDO abstract.

(Continued)

*Primary Examiner* — Mark Navarro
(74) *Attorney, Agent, or Firm* — Kilpatrick Townsend & Stockton LLP

(57) ABSTRACT

An immunogenic agent which comprises a killed strain of *Burkholderia pseudomallei*, or a combination of components thereof which combination produces a protective immune response in an animal to whom it is administered, and which comprises at least two members selected from the group consisting of (i) a lipopolysaccharide of *Burkholderia pseudomallei*, (ii) a capsular polysaccharide of *Burkholderia pseudomallei* and (iii) a protein of *Burkholderia pseudomallei* or an immunogenic variant thereof or an immunogenic fragment of either of these, or a nucleic acid which expresses said protein, immunogenic variant or immunogenic fragment thereof in a host animal; for use in the prevention or treatment of infection by *Burkholderia pseudomallei* and/or *Burkholderia mallei*.

17 Claims, 4 Drawing Sheets

OTHER PUBLICATIONS

Nierman, et al., 'Structural flexibility in the *Burkholderia mallei* genome,' *Proc. Natl. Acad. Sci.*, 101(39):14246-14251 (2004).

Woo, et al., 'Cloning and characterisation of *malE* in *Burkholderia pseudomallei*,' *J. Med. Microbiol.*, 50:330-338 (2001) XP 002399893.

Anuntagool, et al., 'Antigenic Heterogeneity of Lipopolysaccharide Among *Burkholderia pseudomallei* Clinical Isolates,' *Southeast Asian J. Trop. Med. Public Health*, 31(Suppl. 1):146-152 (2000).

Anuntagool, et al., 'Lipopolysaccharide from Nonvirulent Ara+ *Burkholderia pseudomallei* Isolates Is Immunologically Indistinguishable from Lipopolysaccharide from Virulent Ara− Clinical Isolates,' *Clinical and Diagnostic Laboratory Immunology*, 5(2):225-229 (1998).

Atkins, et al., 'Characterisation of an acapsular mutant of *Burkholderia pseudomallei* identified by signature tagged mutagenesis,' *Journal Medical Microbiology*, 51:539-547 (2002).

Brett, et al., 'Structural and Immunological Characterization of *Burkholderia pseumallei* O-Polysaccharide-Flagellin Protein Conjugates,' *Infection and Immunity*, 64(7):2824-2828 (1996).

Brett, et al., 'Pathogenesis of and immunity to melioidosis,' *Acta Tropica*, 74:201-210 (2000).

Bryan, et al., 'Passive protection of diabetic rats with antisera specific for the polysaccharide portion of the lipopolysaccharide isolated from *Pseudomonas pseudomallei*,' *Can. J. Infect. Dis.*, 5(4):170-178 (1994).

Elvin, et al., 'Protection against Heterologous *Burkholderia pseudomallei* Strains by Dendritic Cell Immunization,' *Infection and Immunity*, 74(3):1706-1711 (2006).

Golovliov, et al., 'Cytokine Expression in the Liver during the Early Phase of Murine Tularemia,' *Infection and Immunity*, 63(2):534-538 (1995).

Healey, et al., Humoral and Cell-Mediated Adaptive Immune Responses Are Required for Protection against *Burkholderia pseudomallei* Challenge and Bacterial Clearance Postinfection, *Infection and Immunity*, 73(9):5945-5951 (2005).

Ho, et al., 'Specificity and Functional Activity of Anti-*Burkholderia pseudomallei* Polysaccharide Antibodies,' *Infection and Immunity*, 65(9):3648-3653 (1997).

Holden, et al., 'Genomic plasticity of the causative agent of melioidosis, *Burkholderia pseudomallei*,' *PNAS*, 101(39):14240-14245 (2004).

Isshiki, et al., Separation of 6-deoxy-heptane from a smooth-type lipopolysaccharide preparation of *Burkholderia pseudomallei*, *FEMS Microbiol. Lett.*, 199:21-25 (2001).

Jakob, et al., 'Activation of Cutaneous Dendritic Cells by CpG-Containing Oligodeoxynucleotides: A Role for Dendritic Cells in the Augmentation of Th1 Responses by Immunostimulatory DNA1,' *The Journal of Immunology*, 161:3042-3049 (1998).

Jones, et al., 'Passive protection against *Burkholderia pseudomallei* infection in mice by monoclonal antibodies against capsular polysaccharide, lipopolysaccharide or proteins,' *J. Med. Microbiol.*, 51:1055-1062 (2002).

Le, et al., 'Safety, tolerability and humoral immune responses after intramuscular administration of a malaria DNA vaccine to healthy adult volunteers,' *Vaccine*, 18:1893-1901 (2000).

Lipman, et al., Rapid and Sensitive Protein Similarity Searches, *Science*, 227:1435-1441 (1985).

Matsuura, et al., 'Biological activities of lipopolysaccharide of *Burkholderia (Pseudomonas) pseudomallei*,' *FEMS Microbiol. Lett.*, 137:79-83 (1996).

Nelson, et al., 'Evaluation of lipopolysaccharide and capsular polysaccharide as subunit vaccines against experimental melioidosis,' *Journal of Medical Microbiology*, 53:1177-1182 (2004).

Reckseidler, et al., 'Detection of Bacterial Virulence Genes by Subtractive Hybridization: Identification of Capsular Polysaccharide of *Burkholderia pseudomallei* as a Major Virulence Determinant,' *Infection and Immunity*, 69(1):34-44 (2001).

Reckseidler-Zenteno, et al., 'The Capsular Polysaccharide of *Burkholderia pseudomallei* Contributes to Survival in Serum by Reducing Complement Factor C3b Deposition,' *Infection and Immunity*, 73(2):1106-1115 (2005).

Reed and Muench, 'A Simple Method of Estimating Fifty Per Cent Endpoints,' *Am. J. Hygiene*, 27(3):493-497 (1938).

Sizemore, et al., 'Attenuated bacteria as a DNA delivery vehicle for DNA-mediated immunization,' *Vaccine*, 15(8):804-807 (1997).

Titball, et al., 'Vaccination against bubonic and pneumonic plague,' *Vaccine*, 19(30):4175-4184 (2001).

Ulett, et al., 'A model of immunity to *Burkholderia pseudomallei*: unique responses following immunization and acute lethal infection,' *Macrobes and Infection*, 7:1263-1275 (2005).

Velez, et al., *Trans. R. Soc. Trop. Med. Hyg.*, 99(8):593-598 (2005).

Warawa, et al., 'Melioidosis vaccines,' *Expert Rev. Vaccines*, 1(4):477-482 (2002).

NCBI Database Accession No. YP_110850, Sep. 1, 2004.
NCBI Database Accession No. YP_110888, Sep. 1, 2004.
NCBI Database Accession No. YP_111684, Sep. 1, 2004.
NCBI Database Accession No. YP_111854, Sep. 1, 2004.
UniProt Database Accession No. Q62CY2, Oct. 25, 2004.
UniProt Database Accession No. Q63M21, Oct. 25, 2004.
NCBI Database Accession No. BX571965, bases 1804529-1805555 & 2743305-2743985, Sep. 1, 2004.
NCBI Database Accession No. BX571966, bases 2898490-2900025, Sep. 1, 2004.
NCBI Database Accession No. CAH35556, Sep. 1, 2004.
NCBI Database Accession No. CAH39624, Sep. 1, 2004.
NCBI Database Accession No. CAH 36280, Sep. 1, 2004.
NCBI Database Accession No. CP000010, bases 338153-339688 & 1351990-1353016, Sep. 22, 2004.
NCBI Database Accession No. CP000010, bases 338153-339688, Sep. 22, 2004.
NCBI Database Accession No. AAU47551, Sep. 22, 2004.
NCBI Database Accession No. AAU45954, Sep. 22, 2004.
NCBI Database Accession No. AAU47807, Sep. 22, 2004.

Atkins, H.S. et al., "The identification and evaluation of ATP binding cassette systems in the intracellular bacterium *Francisella tularensis*," Research in Microbiology, Feb. 8, 2006, vol. 157, pp. 593-604.

Harding, S. et al., "The identification of surface proteins of *Burkholderia pseudomallei*", Vaccine 2007, vol. 25, pp. 2664-2672.

Woo, P. et al., "groEL Encodes a Highly Antigenic Protein in *Burkholderia pseudomallei*", Clinical and Diagnostic Laboratory Immunology, Jul. 2001, vol. 8, No. 4, pp. 832-836.

\* cited by examiner

IMMUNOGENIC AGENTS AGAINST *BURKHOLDERIA PSUDOMALLEI* AND/OR *BURKHOLDERIA MALLEI*, COMPRISING LIPOPOLYSACCHARIDE, CAPSULAR POLYSACCHARIDE AND/OR PROTEINS FROM *BURKHOLDERIA PSEUDOMALLEI*

CROSS REFERENCE TO RELATED APPLICATIONS

This application is the U.S. national phase of International Application No. PCT/GB2006/003628 filed on Oct. 2, 2006 and published in English on Apr. 5, 2007 as International Publication No. WO 2007/036735, which application claims priority to Great Britain Application No. 0519871.8 filed on Sep. 30, 2005, the contents of both of which are incorporated herein by reference.

The present invention relates to immunogenic agents which are useful as prophylactic or therapeutic vaccines against infection by *Burkholderia pseudomallei* and/or *Burkholderia mallei*.

*Burkholderia pseudomallei* is the causative agent of melioidosis, a severe disease of humans and animals. The bacterium is present in the environment, mainly in South East Asia, Northern Australia, parts of Africa, South and Central America. Although melioidosis has historically been considered to be a relatively rare disease it is being diagnosed in an increasing number of countries and with an increasing frequency. This is probably due to a combination of factors, such as recent improvements in diagnostic techniques, a greater awareness of the disease and an increase in global travel from areas of the world where melioidosis is endemic.

Melioidosis can present in a number of forms which have been described as acute septicaemic, acute pulmonary, sub-acute and chronic diseases. In some cases a persistent sub-clinical infection is established with the subsequent ability to become septicaemic. The factors which influence the outcome of disease are not known, although it has been suggested that differences in the virulence of different strains might contribute to the clinical outcome of disease. In addition, melioidosis is most frequently seen in diabetics, those with impaired cellular immunity or those with a history of drug or alcohol abuse, suggesting that differences in the immunological status of the host might also influence the outcome of the disease.

Currently no vaccine exists to protect against melioidosis. *B. pseudomallei* has previously been shown to produce two types of lipopolysaccharide (LPS), termed OPSI and OPSII, and a capsular polysaccharide [Y. Isshiki et al, FEMS Microbiol. Lett. 2001, 199, 21-25, S. Reckseidler et al. Infect. Immun. 2001, 69(1) 34-44].

The LPS of *B. pseudomallei* has been shown to be biologically active and capable of stimulating murine macrophages [M. Matsuura et al. FEMS Microbiol. Lett 1996, 137, 79-83]. Further studies have shown that LPS is capable of stimulating an immune response in the murine model of disease. Polyclonal antisera raised against the LPS was found to be passively protective against challenge with *B. pseudomallei* [M. Nelson et al. Journal of Medical Microbiology 2004, 53 (12) 1177-1182]. Conjugates of LPS and *B. pseudomallei* flagellin have been proposed and evaluated as putative vaccine candidates [P. Brett et al. Infect Immun. 1996, 64(7) 2824-2828].

There is also evidence that capsular polysaccharides play a role in the virulence of both Gram-negative and Gram-positive bacteria and are important in protecting the bacteria from host defense systems. Insertional inactivation of the capsule biosynthetic pathway results in the production of an avirulent *B. pseudomallei* strain [Reckseidler et al supra., Atkins et al. Journal Medical Microbiology 2002, 51, 539-547]. Capsular polysaccharide is produced by both *B. pseudomallei* strains K96243 and 576, and has been shown to be a potential vaccine candidate [Nelson et al. supra].

It has been previously demonstrated that passive administration of monoclonal antibody raised against protein antigens of *B. pseudomallei* can confer protection [S. M. Jones et al. Journal of Medical Microbiology 2002, 51 (12) 1055-1062].

Although antisera raised against these conjugate vaccines is protective in animal studies, active immunisation with the conjugate has not been reported.

Inactivated vaccines have been used previously to provide protection against a number of diseases including typhoid, whooping cough, polio and rabies and demonstrate that vaccination against individual diseases is possible given the correct stimulation of the immune system by antigen. However, it is not possible to predict whether, in any particular case, such preparations will provide the sort of stimulation, which would lead to protection, and there have been many instances where killed whole cell vaccines have proved ineffective.

For instance, killed whole-cell preparations of mycobacterium have historically been regarded as inefficient vaccines against for example TB, and so the live attenuated vaccine, bacilli Calmette-Guerin (BCG) is the registered vaccine. Killed whole cell vaccine against *Yersinia pestis* has been found to offer poor protection against pneumonic disease (R. W. Titball et al. Vaccine 2001, 19(30) 4175-84. A recent study using a killed whole-cell Lishmania amazonensis vaccine has shown that it provides no protection against disease (I. D. Velez et al., Trans. R Soc Trop. Med Hyg, 2005, 99(8):593-8).

Generally, vaccines which induce specifically antibody responses such as killed whole cell vaccines are regarded as being ineffective against intracellular pathogens such as *Burkholderia*.

However, the applicants investigated whether immunisation with killed whole cells of *B. pseudomallei* can protect mice against experimental melioidosis, and found good results.

The model used provided for an assessment of the relative roles of capsule, LPS and surface proteins in protection against disease, and so provide improved conjugate vaccines also.

According to the present invention, there is provided an immunogenic agent which comprises a killed strain of *Burkholderia pseudomallei*, or a combination of components thereof which combination produces a protective immune response in an animal to whom it is administered, and which comprises at least two members selected from the group consisting of (i) a lipopolysaccharide of *Burkholderia pseudomallei*, (ii) a capsular polysaccharide of *Burkholderia pseudomallei* and (iii) an immunogenic protein of *Burkholderia pseudomallei* or an immunogenic variant thereof or an immunogenic fragment of either of these, or a nucleic acid which expresses said protein, immunogenic variant or immunogenic fragment in a host animal; for use in the prevention or treatment of infection by *Burkholderia pseudomallei* and/or *Burkholderia mallei*.

Immunogenic agents according to the invention have been found to provide good protection against challenge by *B. pseudomallei* species in animal models, and can therefore form the basis of prophylactic or therapeutic vaccines in animals such as humans.

Preferably, the protective response is protective for at least 20 days post-challenge or infection by *Burkholderia pseudomallei* and/or *Burkholderia mallei*.

In a particular embodiment of the invention, the immunogenic agent is a killed strain of *Burkholderia pseudomallei*, preferably one which includes a capsular polysaccharide.

In one aspect of the invention, the killed strain of *Burkholderia pseudomallei* produces a protective immune response in an animal to whom it is administered. Preferably, the protective response is protective for at least 20 days post-challenge or infection by *Burkholderia pseudomallei* and/or *Burkholderia mallei*.

The strain may be killed by conventional methods for example by heat treatment, freeze-thaw treatment, sonication, sudden pressure drop or treatment using an inactivating agent such as formalin, azide, sodium hypochlorite, phenol, saponin, detergent (such as non-ionic detergent) lysozyme, propiolactone and in particular betapropiolactone, binary ethyleneimine (U.S. Pat. No. 5,565,205) or Thimerosal (U.S. Pat. No. 5,338,543). Preferably the strain is killed using a treatment which leaves at least some surface molecules intact.

In particular, however, the immunogenic agent is a heat-killed strain.

It is suitably prepared by heating cultures of *B. pseudomallei* to temperatures of from 50-90° C. for a period sufficient to ensure that all cells are inactive. This can be tested using routine methods as illustrated hereinafter. In particular, heating a culture of *B. pseudomallei* to a temperature of about 80° C. for a period of about 3 hours has been found to result in complete inactivation.

Suitable strains include any of the available strains irrespective of the lipopolysaccharide serotype. Examples of known strains include *B. pseudomallei* K96243 (Proc. Natl. Acad. Sci. USA (2004) 01 (39)14240-14245) and *B. pseudomallei* 576. Examples are *B. pseudomallei* strains are available for example from the National Collection of Type Cultures, Central Public Health Laboratory, 61 Colindale Avenue, London NW9, 5HT UK where examples include those stored as NCTC 4845, NCTC 12939, NCTC13177, NCTC13178 and NCTC 13172, but others may be isolated from natural sources for example from patients suffering from *B. pseudomallei* infection, or from environmental sources such as soil samples.

In one embodiment the strain is one which has an atypical LPS serotype (OPSII), such as *B. pseudomallei* 576.

In another embodiment, the strain is one which has a typical LPS serotype (OPSI) such as *B. pseudomallei* K96243, the genome sequence of which is available.

In an alternative embodiment of the invention, the immunogenic agent is a combination of *Burkholderia pseudomallei* components comprising at least two members of the group selected from the group consisting of (i) a lipopolysaccharide of *Burkholderia* pseudomallei, (ii) a capsular polysaccharide of *Burkholderia* pseudomallei and (iii) an immunogenic protein of *Burkholderia* pseudomallei or an immunogenic variant thereof, or an immunogenic fragment of either of these, or a nucleic acid which expresses said immunogenic protein, variant or fragment in a host animal.

It has been found that this group of components can act synergistically together, enhancing the protective effect that would be obtained using the components individually.

In one embodiment, the combination comprises a lipopolysaccharide and a capsular polysaccharide of *Burkholderia pseudomallei*.

In a further embodiment, the combination comprises a lipopolysaccharide and an immunogenic protein of *Burkholderia* pseudomallei or an immunogenic variant thereof, or an immunogenic fragment of either of these, or a nucleic acid which expresses said immunogenic protein, variant or fragment in a host animal.

Preferably all three components are present and so the immunogenic agent comprises (i) a lipopolysaccharide of *Burkholderia pseudomallei*, (ii) a capsular polysaccharide of *Burkholderia pseudomallei* and (iii) an immunogenic protein of *Burkholderia pseudomallei* or an immunogenic variant thereof, or an immunogenic fragment of either of these, or a nucleic acid which expresses said immunogenic protein, variant or fragment in a host animal.

As used herein, the expression "variant" refers to sequences of amino acids which differ from the base sequence from which they are derived in that one or more amino acids within the sequence are substituted for other amino acids, but which retain the ability of the base sequence to produce an immunogenic response which recognises epitopes of *B. pseudomallei*. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide. Suitably variants will be at least 70% identical, for instance at least 75% identical, especially at least 80% identical. In particular variants will be at least 90% identical, and preferably at least 95% identical to the base sequence.

Identity in this instance can be judged for example using the BLAST program or the algorithm of Lipman-Pearson, with Ktuple:2, gap penalty:4, Gap Length Penalty:12, standard PAM scoring matrix (Lipman, D. J. and Pearson, W. R., Rapid and Sensitive Protein Similarity Searches, Science, 1985, vol. 227, 1435-1441).

The term "fragment" refers to any portion of the given amino acid sequence, which includes an epitope and so has immunogenic activity. Fragments will suitably comprise at least 5 and preferably at least 10 consecutive amino acids from the basic sequence.

The combination may comprise more than one lipopolysaccharide, and in a particularly embodiment, it will contain a *B. pseudomallei* lipopolysaccharide of each of the two known serotypes, OPSI and OPSII as described above.

Where the combination includes component (iii) above, this is suitably one or more immunogenic proteins of *Burkholderia* pseudomallei or an immunogenic variant thereof, or an immunogenic fragment of either of these. Preferably component (iii) comprises one or more immunogenic proteins of *Burkholderia* pseudomallei.

Suitable proteins are in particular surface proteins. Thus in a particular embodiment, the combination will comprise an immunogenic surface protein of *Burkholderia pseudomallei* or an immunogenic variant thereof, or an immunogenic fragment of either of these, or a nucleic acid which expresses said immunogenic surface protein, variant or fragment in a host animal Particular surface proteins include ABC transporter proteins (for example as described in International Publication No. WO 2006/109071) porins, pili, adhesins, ion acquisition proteins, or components of the type 3 secretion system.

The immunogenicity of any particular protein can be determined using routine methods as would be apparent to the skilled person.

The selection of specific proteins for testing in this way may alternatively be determined by examination of the proteome of the *B. pseudomallei* species, derivable from the known genomic sequences, using for instance the method described in WO 03/073351.

Alternatively, *B. pseudomallei* proteins can be made or isolated and tested using routine methods to ensure that they are immunogenic.

In a particularly preferred embodiment, the combination comprises more than one such protein or immunogenic variant, or fragment of either of these.

In an alternative embodiment, the combination comprises a nucleic acid which expresses said immunogenic protein, variant or fragment in a host animal. In this instance, the nucleic acid might be incorporated into an expression vector, in particular a pharmaceutically acceptable expression vector such as a viral vector such as vaccinia (for instance, the Lister strain), or adenovirus vectors which are suitably attenuated, or a bacterial expression vector such as an attenuated *Salmonella* strain for instance attenuated strains of *S. typhi* or *S. typhimurium* such as SL3261. Nucleic acids may also be in the form of a plasmid or "naked DNA" vaccine. Suitable plasmids include those known in the art and many are commercially available.

Immunogenic agents of the invention are suitably administered in the form of one or more pharmaceutical compositions, which suitably further comprises a pharmaceutically acceptable carrier.

Where the immunogenic agent comprises a combination as described above, individual components may be administered separately or together, but are suitable formulated together in a single dosage unit.

The nature of the carrier will vary depending upon the nature of the immunogenic agent, the mode of administration selected etc. in accordance with normal pharmaceutical procedure.

Suitable carriers are well known in the art and include solid and liquid diluents, for example, water, saline or aqueous ethanol. The liquid carrier is suitably sterile and pyrogen free.

The compositions may be suitable for oral use (for example as tablets, lozenges, hard or soft capsules, aqueous or oily suspensions, emulsions, dispersible powders or granules, syrups or elixirs), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular or intradermal dosing) or as a suppository for rectal dosing.

They will be combined with pharmaceutically acceptable excipients, such as inert diluents, granulating or disintegrating agents, binding agents, lubricating agents, preservative agents and anti-oxidants. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Where the immunogenic agent includes a nucleic acid element which is in the form of "live vaccine", this will be formulated to ensure that they produce the desired effect. For example, where the vaccine comprises a viral vector, they may be contained within formulations suitable for parenteral administration or, when possible, for oral administration, inhalation or insufflation.

Where bacterial vectors such as attenuated *Salmonella* strains are used to deliver the nucleic acid which encodes a protein element of the immunogenic agent, they are suitably formulated for oral administration.

In particular, where the vaccine comprises a naked DNA vaccine, they will be formulated such that they are suitable for parenteral administration, for example by combination with liquids such as saline. These compositions are preferably formulated for intramuscular injection, although other means of application are possible as described in the pharmaceutical literature, for example administration using a Gene Gun, (Le et al., (2000), Vaccine 18, 1893-1901). Oral or intra-nasally delivered formulations are also possible. Such formulations include delivery of the plasmid DNA via a bacterial vector such as species of *Salmonella* or *Listeria* (Sizemore et al (1997). Vaccine 15, 804-807).

Dosages of the vaccine used in any particular case will depend upon factors such as the particular protein used or expressed by the vaccine, the nature of the patient receiving the treatment etc. and will be determined in any particular case in accordance with conventional clinical practice. Generally speaking however, in general, the immunogenic agent will be administered in an amount of from 0.5 mg to 75 mg per kg body weight. Where the immunogenic includes a "live" vaccine component, such as a virus vector, dosages of the vector may be in the range of from $10^4$-$10^{12}$ pfu (pfu=particle forming units).

The compositions of the invention may further additional other active components. For example, the other component may comprise an adjuvant which enhances the host's immune response, and/or the polypeptide may be combined with an antigen giving protective immunity against a different pathogen to form a multivalent vaccine in order to increase the benefit-to-risk ratio of vaccination.

In a particularly preferred embodiment, the other active component comprises an adjuvant which enhances the host's immune response and in particular promotes a cellular immune response, such as a CD8+, a CD4+ and/or a Th1 response.

Adjuvants which may achieve these effects include cytokines such as interleukins and interferons. In particular, the other component comprises a cytokine such as an interleukin, which acts as a Th-1 adjuvant. A particularly preferred interleukin for inclusion in the vaccines of the invention is IL-12, which has been shown to drive the expansion of a protective Th-1 cell response during early murine tularemia (Golovliov I, et al. (1995). Infection and Immunity 63(2):534-8).

Other types of pharmaceutically adjuvant include Freund's incomplete adjuvant, aluminium compounds such as aluminium hydroxide, polycationic carbohydrates such as chitosan and derivatives thereof, for example as described in WO00/56362, or adjuvants described in WO00/56361 or WO00/56282.

However, for reasons discussed in more detail below, a particularly preferred class of adjuvants are those which activate or stimulate antigen-presenting cells, such as dendritic cells. These can evoke in particular long lasting protective immune responses against a range of strains. Examples of such adjuvants are Toll-like receptor (TLR) ligands such as CpG oligonucleotides (for example as described in U.S. Pat. No. 6,429,199), bacterial lipopolysaccharides or lipoproteins. Where the immunogenic reagent includes as a component a lipopolysaccharide derived from *B. pseudomallei*, the Toll-like receptor ligand used as the adjuvant, is suitably other than a lipopolysaccharide derived from *B. pseudomallei*.

These are suitably coadministered or even linked to the immunogenic reagents described above, which may in particular be recombinant *B. pseudomallei* proteins, in order to enhance the response of the hosts antigen-presenting cells, so as to produce synergistic levels of protection.

In a further particular embodiment however, the immunogenic agent described above may be combined with antigen-presenting cells. This combination is then co-administered.

Antigen-presenting cells are instrumental in producing an immune response and operate by various mechanisms. They include macrophages and dendritic cells.

Dendritic cells (DC's) are specialised antigen presenting cells that have a central role in initiating T-cell responses. Immature DC's engulf pathogens, initiating a process of maturation, which includes their migration to lymphoid organs and culminates in enhanced expression of MHC II-peptide complexes and various co-stimulatory molecules. They convey information regarding the nature of the microbial stimulus to T-cells and direct the development of polarised T-cell responses along either the type 1 or type 2 pathways.

The applicants have found that cultured dendritic cells pulsed with immunogenic reagents described above, and in particular killed B. pseudomallei strains such as heat killed B. pseudomallei 4845 or K96243 can be used to immunise animals and evoke both cell mediated and humoral immune responses in the recipients. This gives rise to ex-vivo therapeutic options.

As used herein the term "ex-vivo" describes a procedure that is carried out on a sample taken from a patient, the sample being returned to the patient after treatment.

In a particular embodiment therefore, the invention provides an immunogenic reagent as described above for use in the preparation of a medicament for administration to antigen-presenting cells (APC) of a patient, for the activation of the immune response of said patient.

Compositions comprising these immunogenic reagents and antigen-presenting cells such as dendritic cells are also novel and form a further aspect of the invention.

Adjuvants such as CpG oligodeoxynucleotides (unmethylated cytidine-guanosine dinucleotides flanked by patterns of bases as described for example in U.S. Pat. No. 6,429,199) can be used either to enhance APC and particularly DC maturation in vitro or as an adjuvant when administered to animals at the time they are immunised with antigen pulsed DC. In vitro and in vivo exposure of DC to CpG causes upregulation of MHC II and expression of the co-stimulatory molecules CD40, CD80 and CD86.

Cohorts of animals immunised with dendritic cells were taken forward for virulent challenge with different strains of *B. pseudomallei* and protection against parenteral challenge was demonstrated.

An ex-vivo medicament of this type will advantageously allow the activation of antigen presenting cells to be controlled and monitored, thus providing a patient with transfected cells which will increase the patients immune response whilst also removing existing problems with vaccines such as dilution in body fluids and chemical and enzymatic degradation in vivo.

The ability of DC pulsed with heat killed *B. pseudomallei* to induce proliferation of naïve mouse spleen cells has been demonstrated as illustrated below. The magnitude of proliferative responses was much higher in animals which had been immunised with antigen pulsed DC. This data shows that DC immunisation has the potential to induce antigen specific memory immune responses in recipient animals. Additionally, significantly increased numbers of interferon-γ producing cells in animals immunised with CpG treated heat killed *B. pseudomallei* pulsed DC correlates with data from other studies involving the use of CpG ODN in which enhanced IFN-γ production has been seen.

Elevated levels of IFN-γ correlate with protection against challenge in murine models of melioidosis and the use of CpG-matured, *B. pseudomallei* pulsed DC was found to enhance IFN-γ production and also to result in significantly enhanced protection.

Low titres of antigen specific IgG in serum of vaccinees were found but this may have been due to the very small amounts of antigen delivered by DC immunisation, as it is known that relatively large amounts of antigen are required in order for a robust antibody response to be mounted. The use of CpG either in DC maturation or as an adjuvant at the point of DC immunisation increased antibody titres significantly compared with the non-CpG treated group, as has been seen in other studies. This could have contributed to the robust protection seen in the CpG treated groups, as antibody may have an important role in defence against melioidosis, with high circulating titres of antigen specific monoclonal antibody being shown to provide protection against challenge.

The importance of antibody is likely to be limited to the early stages of an infection however, before the bacteria are able to gain access to the intra-cellular niche in which they are known to thrive. Once the bacteria have established an intracellular infection cell mediated immune mechanisms are required for efficient eradication of the pathogen.

A DC immunisation strategy is able to evoke cell-mediated immune mechanisms, as evidenced by increased IFN-γ production and proliferation of spleen cells in response to antigen stimulation in vitro, and these effectors were clearly contributing to the high levels of challenge survival, which the applicants found.

When animals were immunised with DC matured in the presence of CpG 1826 and then challenged with *B. pseudomallei* K96243 there were 9 of 10 survivors, while when CpG 1826 was used as an adjuvant there were 7 of 10 survivors. These survival rates are significantly better than those seen when control non-CpG ODN was used to mature the DC's (3 of 8 survivors) and 2 of 10 survivors when DC vaccination alone was used ($p<0.01$ and $p<0.001$ respectively). Challenging similarly immunised animals with *B. pseudomallei* strain 4845 revealed a similar pattern of resistance, with CpG matured DC immunisation giving 7 of 10 survivors, significantly better ($p<0.02$) than DC immunisation alone.

Challenge with strain 576 again gave a higher rate of survival in animals immunised with CpG treated DC, with significantly improved protection compared with naïve controls ($p<0.0001$).

The ability of the DC immunisation strategy to evoke protective immune responses to heterologous strains of *B. pseudomallei* is very encouraging as the wide variety of strains found in human infections obviously have different characteristics enabling induction of many different forms of disease and lengthy latency periods. A vaccination strategy is required that will be able to protect against this wide variety of strains and induce long lasting immunity, and a strategy based upon the use of APC would fulfill these requirements.

However, from a practical viewpoint, this is unlikely to be applicable as a widespread vaccination strategy since each individual would require a personalised syngeneic vaccine.

A vaccine that can stimulate DC in situ to evoke the protective immune responses can be produced for example by means of a formulation carrying immunogenic reagents as described above, and in particular recombinant *B. pseudomallei* antigens, as well as Toll-like receptors (TLR) ligands. Binding of the TLR ligands would activate the DC initiating the process of antigen uptake, processing and presentation required in the generation of a protective immune response.

Killed strains of *Burkholderia pseudomallei* may be novel and these form a further aspect of the invention. Particular killed strains are those described above, for example wherein the strain is one which includes a capsular polysaccharide, and/or is a heat-killed strain.

In a further aspect, the invention comprises a method of preventing or treating infection by *Burkholderia pseudomallei* and/or *Burkholderia mallei*, which method comprises administering to an animal, in particular a human, an immunogenic agent or a composition as described above.

The immunogenic agent or composition is suitably administered in the context of a method for preventing infection by *Burkholderia* pseudomallei and/or *Burkholderia mallei*, i.e. as a prophylactic vaccine.

In yet a further aspect, the invention provides an immunogenic agent as described above for use in the preparation of a medicament for the prevention or treatment of infection by *B. pseudomallei* and/or *B. mallei*.

Preferred immunogenic agents are also as set out above.

The invention will now be particularly described by way of example with reference to the accompanying diagrammatic drawings in which.

Figure 1:
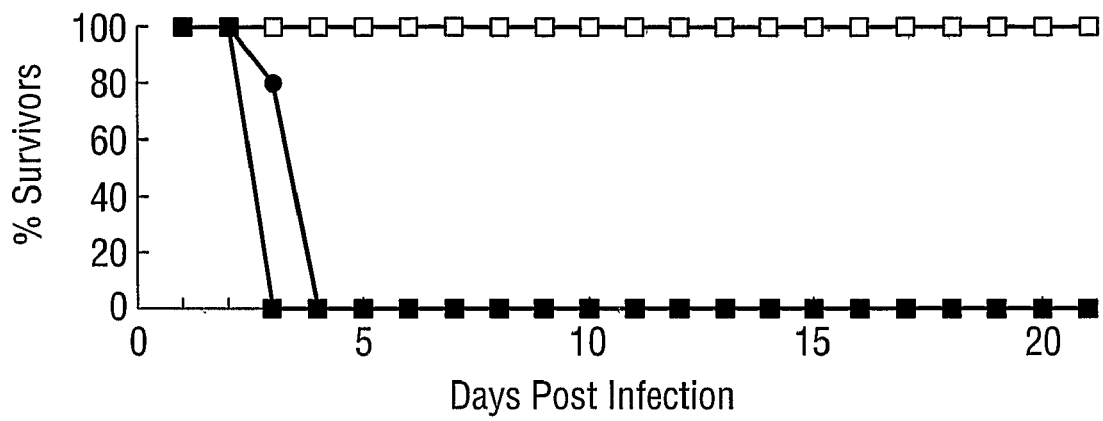
FIG. 1 is a graph showing the survival of immunized mice following intra-peritoneal challenge with a homologous strain of *B. pseudomallei*: Control mice challenged with 100MLD *B. pseudomallei* strain K96243(■) or strain 576 (●); mice immunized with killed K96243 cells and challenged with 100MLD K96243(□); and mice immunized with killed 576 cells and challenged with 100MLD 576 (○)
Figure 2:
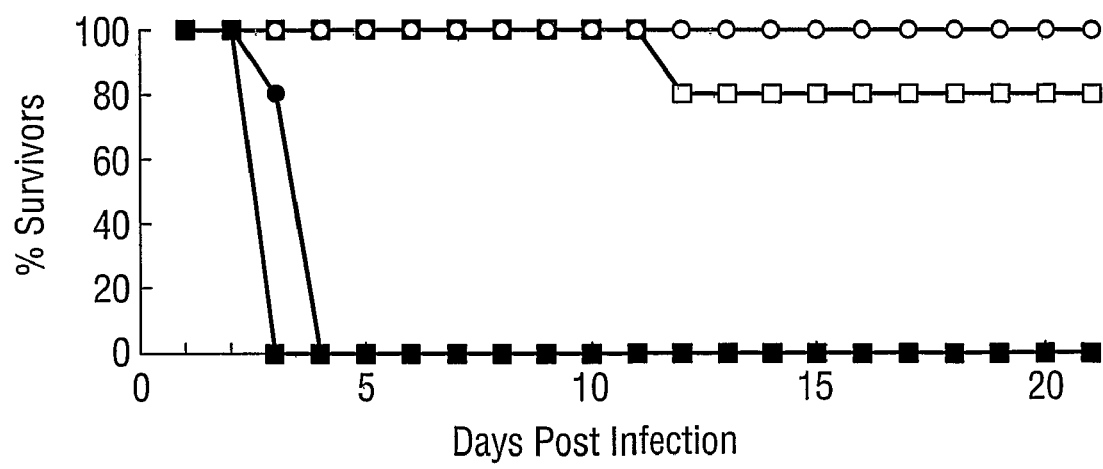
FIG. 2 is a graph showing the survival of immunized mice following intra-peritoneal challenge with a heterologous strain of *B. pseudomallei*: Control mice challenged with 100MLD *B. pseudomallei* strain K96243(■) or strain 576 (●); mice immunized with killed K96243 cells and challenged with 100MLD K576(□); and mice immunized with killed 576 cells and challenged with 100MLD K96243576 (○)
Figure 3:
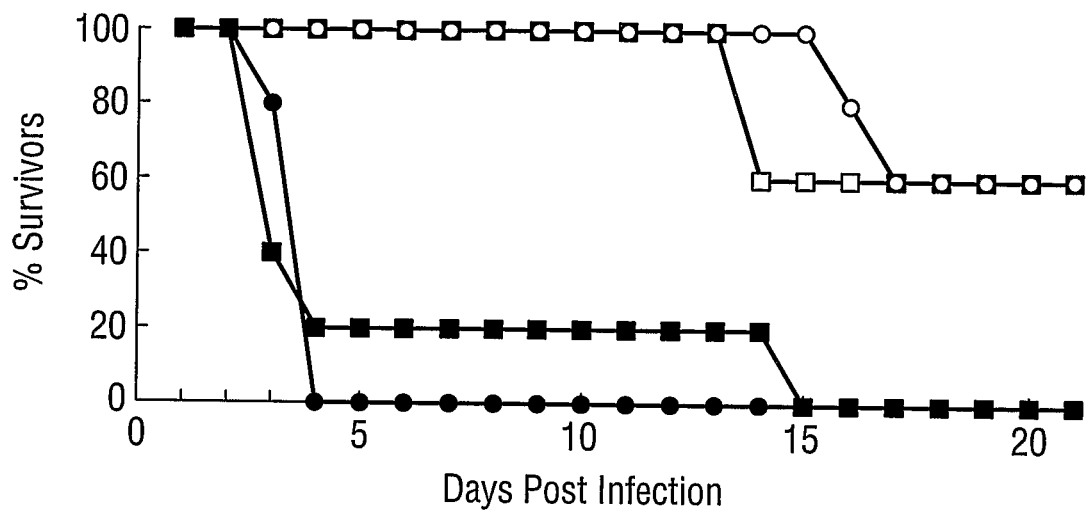
FIG. 3 is a graph showing the survival of mice immunized with 1E10 cells after intra-peritoneal challenge with *B. pseudomallei* strain K96243 or strain 576: Control mice challenged with 100MLD *B. pseudomallei* strain K96243(■) or strain 576(●); mice immunized with killed 1E10 cells and challenged with 100MLD K96243(□); and mice immunized with killed 1E10 cells and challenged with 100MLD 576(○)
Figure 4:
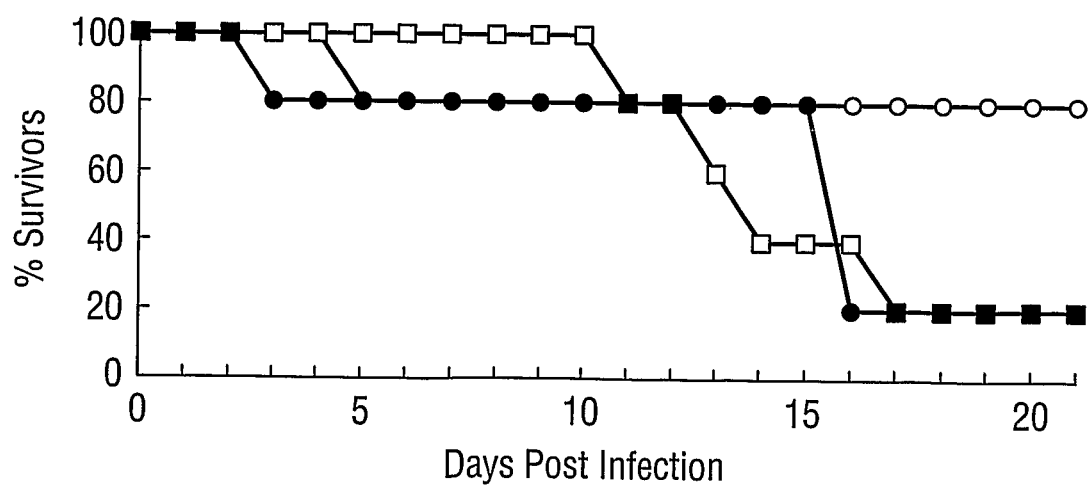

FIG. 4 is a graph showing the survival of control mice ●) or mice immunized with proteinase K treated 1E10 cells (□) or proteinase K treated 576(○) after intra-peritoneal challenge with 100 MLD *B. pseudomallei* strain 576.

Figure 5:
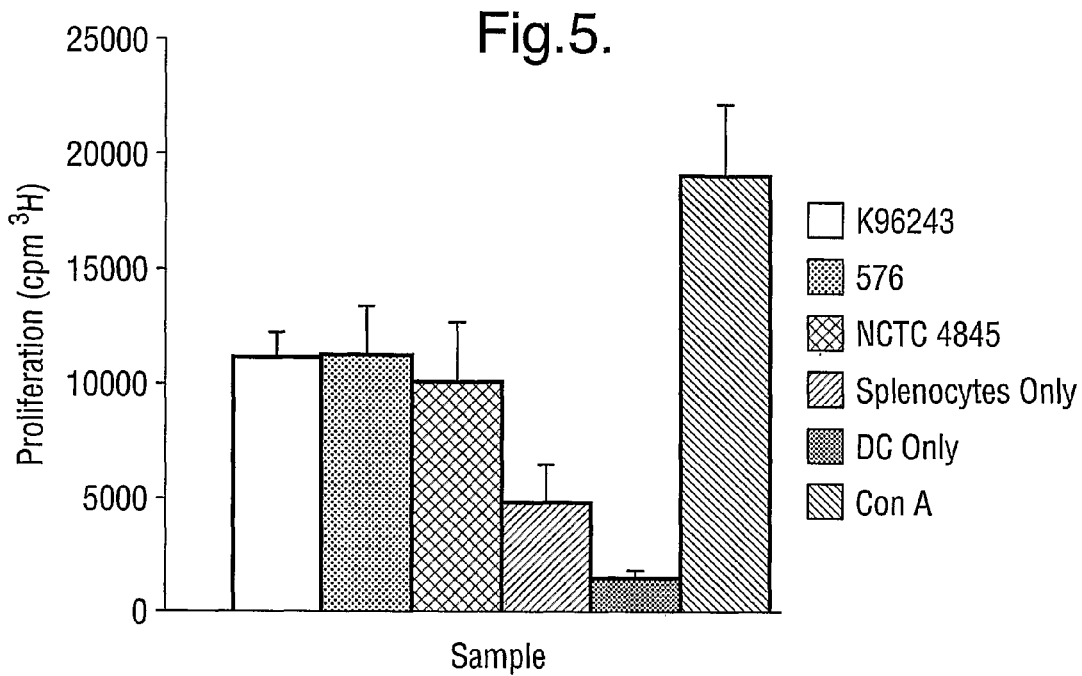
Figure 6:
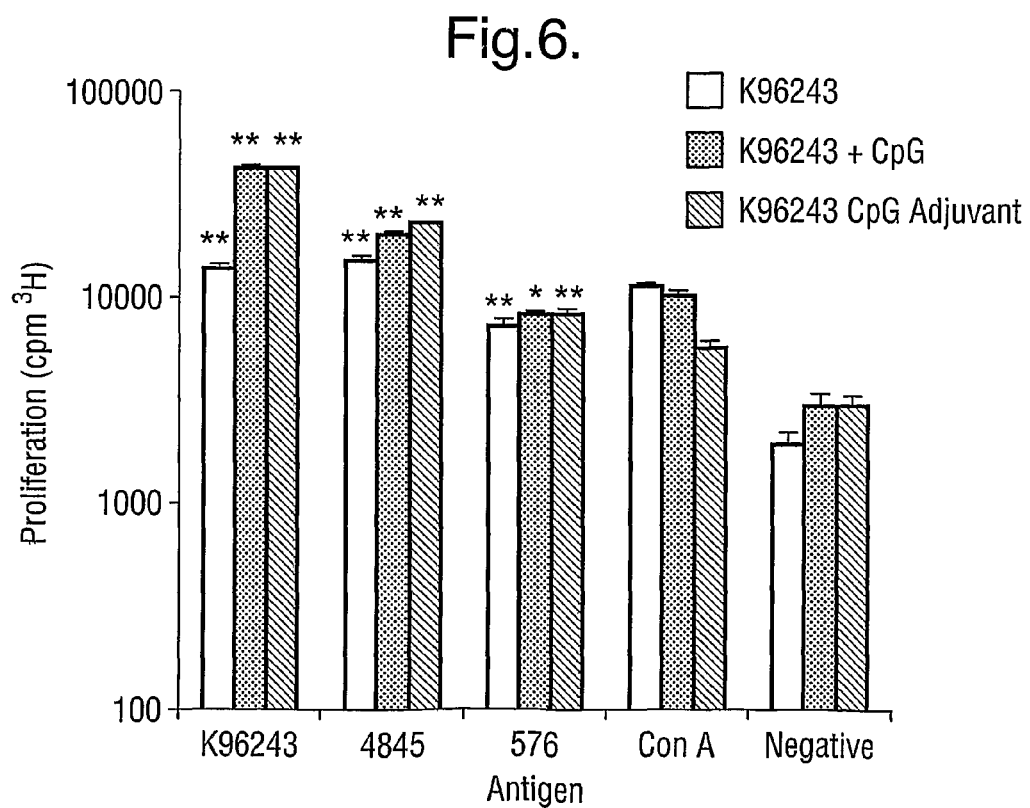
Figure 7:
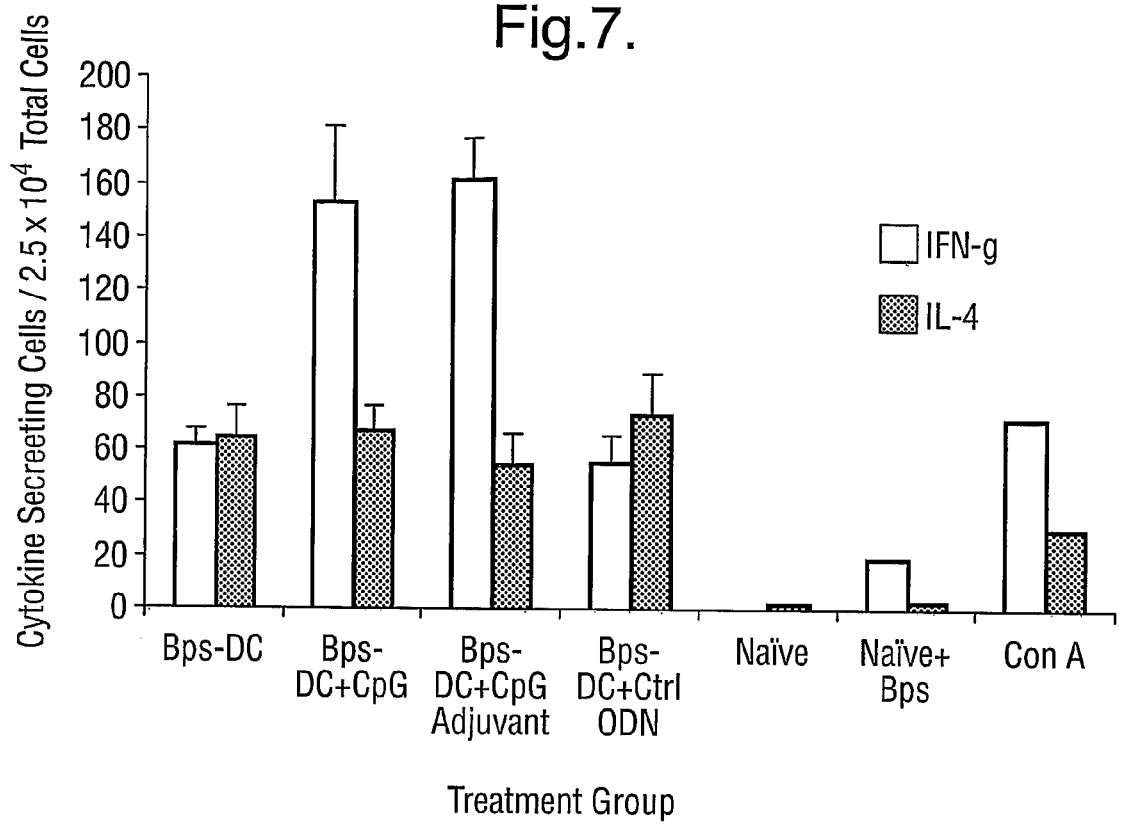
Figure 8:
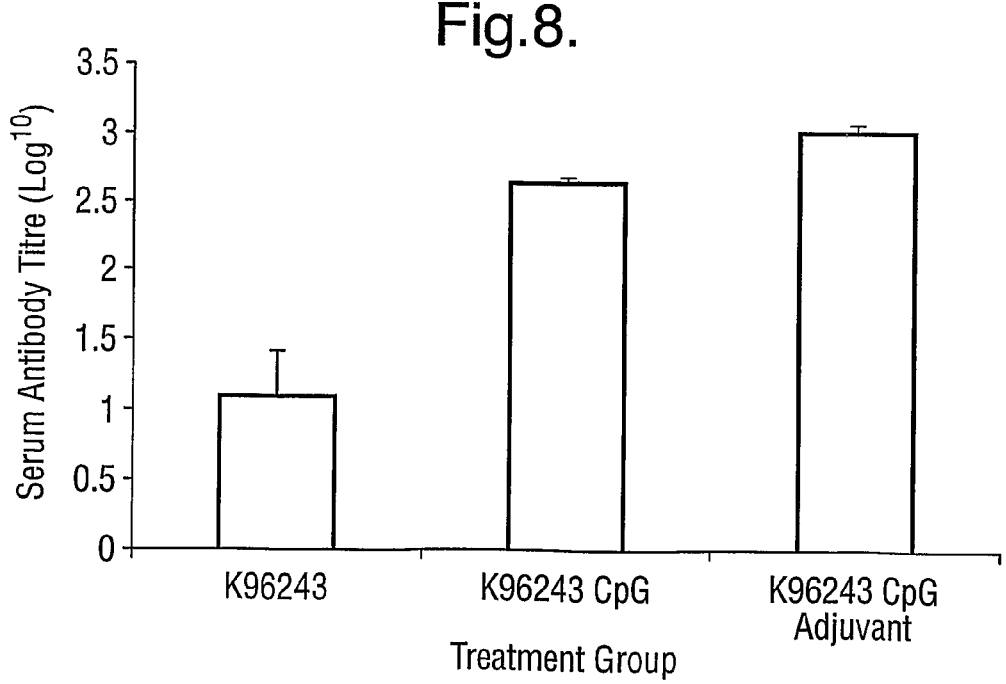

FIG. 5 is a graph showing the proliferation of splenocytes from naive mice stimulated in vitro with DC pulsed with either *B. pseudomallei* K96243, NCTC 4845 or strain 576. Proliferation of cells stimulated by antigen pulsed DC was greater than the proliferation of unstimulated splenocytes or DC alone, irrespective of which strain of heat killed *B. pseudomallei* was used in the assays. Each bar represents the mean of 5 individuals ±SD;

FIG. 6 is a graph showing proliferation of spleen cells from mice immunised with *B. pseudomallei* K96243 pulsed DC, matured in the presence or absence of CpG 1826, or administered with CpG 1826 as an adjuvant, in response to various strains of *B. pseudomallei*. The data show significantly enhanced proliferation in vitro of in vivo primed cells to different strains of *B. pseudomallei*, compared with unstimulated in vivo primed cells in vitro. Each bar represents the mean of 5 individuals ±SD. Statistically significant differences between immunised and control samples are indicated: * $p<0.001$, ** $p<0.0001$;

FIG. 7 is a graph showing numbers of cytokine secreting cells per $10^4$ total spleen cells. Animals were immunised with DC matured with antigen or, antigen and CpG 1826 (6 µg ml$^{-1}$) or, control ODN (6 µg ml$^{-1}$) or DC matured with antigen only and injected with CpG 1826 (75 µg per mouse). Maturation of DC with CpG and use of CpG as an adjuvant significantly increased ($p<0.05$) the numbers of IFN-γ secreting spleen cells compared to the other treatment groups. No effect was seen on the numbers of IL-4 secreting cells in any treatment group;

FIG. 8 is a graph showing serum antibody responses in animals immunised with either DC pulsed with heat killed *B. pseudomallei* K96243 or, DC pulsed with heat killed bacteria in the presence of CpG 1826 (6 µg ml$^{-1}$), or DC pulsed with heat killed bacteria with CpG 1826 co-administered as an adjuvant (75 µg). Each bar represents the mean of 10 individuals with SEM. The CpG treated groups produced significantly more antibody ($p<0.01$) than the DC only treated group.

EXAMPLE 1

Preparation and Use of Heat Killed Strains of *B. pseudomallei*

Chemicals, Enzymes and Bacterial Strains

*B. pseudomallei* stains 576 and K96243 were used for this study unless otherwise stated. *B. pseudomallei* strain 576 was isolated initially from a clinical case of fatal melioidosis in Thailand, *B. pseudomallei* strain K96243 was isolated from a 34 year old female diabetic patient in Khon Kaen hospital in Thailand. All *B. pseudomallei* strains were cultured at 37° C. in Luria Bertani (LB) broth. The capsular mutant strain of *B. pseudomallei* 576, termed *B. pseudomallei* 1E10 has been described previously [T. Atkins et al. Journal Medical Microbiology, 2002, 51, 539-547].

Heat Inactivation of Bacteria

*B. pseudomallei* strains were grown in LB at 37° C. overnight with agitation. The cultures were adjusted to the same absorbance value at 590 nm with PBS and harvested by centrifugation at 5,000 rpm for 15 mins Bacteria were washed once in the original culture volume of PBS, harvested again, and then resuspended in the original volume of PBS. A viable count was performed to determine the number of bacteria heat-killed in cfu/ml. Bacteria were heat inactivated by incubating in a water bath maintained at 80° C. for 3 hours. Inactivated bacteria were then stored at 4° C. Inactivation was confirmed by culturing 10% of each inactivated culture in LB for 7 days at 37° C., then plating out the broth on LB agar plates for 7 days at 37° C. to confirm that no viable bacteria remained.

Animal Studies

Balb/c mice were age-matched, approximately six weeks old females. Stock animals were grouped together in cages of five with free access to food and water and subjected to a 12 h light/dark cycle. After challenge with viable *B. pseudomallei*, the animals were handled under bio-safety level III containment conditions within a half-suit isolator, compliant with British standard BS5726. All investigations involving animals were carried out according to the requirements of the Animal (Scientific Procedures) Act 1986. The median lethal dose (MLD) was calculated by the method of Reed and Muench [Am J. Hygiene, 1938, 27(3) 493-497].

An initial aim was to investigate whether immunisation with heat-killed cells could provide protection against experimental melioidosis.

Immunisation of mice with heat killed bacteria was carried out over a period of five weeks. Each mouse was immunised intra-peritonally (i.p.) with three injections of 100 µl killed bacteria (either strain K96243 or strain 576) of at 1×10⁸ cfu/ml separated by two-week intervals. A period of five weeks elapsed prior to i.p. challenge with the corresponding wild-type bacteria.

The survival of groups of 5 mice immunised with heat-killed *B. pseudomallei* strain K96243 and challenged 2 weeks later with 100 MLD of strain K96243 is summarized in the graph of FIG. 1. The control mice died within four days of challenge. However, complete protection was seen in immunised mice up to day 12, and 80% survival was recorded 3 weeks after challenge.

In the similar experiment, carried out in mice immunised with heat killed, *B. pseudomallei* strain 576 and then challenged with strain 576 similar results were obtained. All of the control animals died by day 4 and all of the immunised animals were alive at the termination of the experiment 3 weeks after challenge (FIG. 1.) This indicates that heat-killed whole cells derived from different strains of *B. pseudomallei* can offer high levels of protection against a homologous challenge.

EXAMPLE 2

Killed Whole Cells Protect Against *B. pseudomallei* Strains Expressing Different Types of LPS.

It has recently been reported that immunisation with LPS is able to provide some protection against experimental melioidosis [M. Nelson et al supra.]. However, it seems unlikely that a single LPS type would provide protection against all strains because two serologically distinct forms of LPS have been identified in different strains of *B. pseudomallei* [N. Anuntagool et al. Clinical and Diagnostic Laboratory Immunology, 1998, 5(2) 225-229]. These different serotypes are represented in this study by strain K96243 (typical LPS or OPSI) and strain 576 (atypical LPS or OPSII).

To investigate the potential for a killed whole cell vaccine to protect against a range of strains of *B pseudomallei* we immunised mice with killed whole cells of strain K96243 or killed whole cells of strain 576 and then challenged with 100 MLD of the heterologous strain, using the same immunization regime described in Example 1.

In both experiments (FIG. 2) the unvaccinated control mice all died within 4 days. None of the immunised mice had died by the end of the experiment (21 days post challenge). Therefore, although immunisation with LPS can provide protection against experimental melioidosis, there are additional protective antigens on the surface of killed cells that provide cross protection against strains belonging to different serotypes.

EXAMPLE 3

The Role of Capsule in Protection

A capsular mutant of strain 576 (strain 1E10 [Atkins et al. supra]) was used to investigate the role of capsular polysaccharide in protection. Mice were immunised with heat-inactivated *B. pseudomallei* strain 1E10 using the immunization regime described in Example 1, and subsequently challenged with 100 MLD of viable *B. pseudomallei* strain 576 or strain K96243. The results are shown in FIG. 3.

Three weeks post challenge 60% of the immunised mice were alive whereas all of the control mice had died.

The level of protection afforded after immunisation with strain 1E10 was lower than that seen after immunisation with the encapsulated parent strain (strain 576). However, it does appear to confirm the role of capsule as a protective antigen, in combination with other cellular components such as protective protein antigens.

EXAMPLE 4

Investigation into the Role of Proteins in Protection

Proteinase K Digestion of Bacteria

Heat-killed suspensions ($8\times10^8$ cfu/ml of the bacteria described in Example 1) were centrifuged for 10 min at 13,000×g, the supernatant was removed and the wet weight of the pellet determined. The pellet was re-suspended in extraction buffer (62.5 mM Tris-HCl pH 6.8, 10% v/v glycerol, 5% v/v β-mercaptoethanol and 3% w/v SDS) at a concentration of 160 mg bacteria/ml buffer. The suspension was incubated at 100° C. for 15 min, mixed and examined for clarity. Clear suspensions were mixed with equal volumes of 2 mg/ml Proteinase-K solution in extraction buffer and heated at 60° C. for 2 hours. The samples were further boiled for 10 min to deactivate the proteinase-K. The solution was then dialysed exhaustively against $dH_20$ using Slide-A-Lyzer dialysis units (Pierce, Rockfor, Ill.).

The heat-killed cells of *B. pseudomallei* strain 576 or strain 1E10 treated with proteinase K, was then used to immunise mice using an immunization regime as described in Example 1. The mice were subsequently challenged with 100 MLD *B. pseudomallei* 576 also as described in Example 1. The survival rate is represented in FIG. 4.

In the control group, one mouse was alive at day 21 post challenge. Similarly, in the group immunised with proteinase K-digested 1E10, one survivor was remaining after 21 days. When proteinase K digested *B. pseudomallei* 576 cells were used for immunisation, 80% survival was observed 21 days post-infection. The difference between the level of protection after immunisation with proteinase K-treated 1E10 cells and proteinase K-treated 576 cells indicates that proteins play a role in providing protection.

The role of each surface component can be assessed by comparing the protection afforded by wild type and the acapsular mutant strain, summarised in Table 1.

TABLE 1

Summary of the roles of polysaccharide or protein surface antigens on protection against challenge with *B. pseudomallei*

| | 100MLD Challenge, Survivors at Day 21(%) | |
|---|---|---|
| Antigens | K96243(typical) | 576(atypical) |
| K96243 (Typical LPS, Capsule, protein | 80 | 100 |
| 576 (Atypical LPS, Capsule, Protein | 100 | 100 |
| 1E10 Atypical LPS, Protein | 60 | 60 |
| Proteinase K treated 576 Atypical LPS, Capsule | ND | 80 |
| Proteinase K treated 1E10 Atypical LPS, | ND | 20 |
| PBS No antigen | 0 | 0 |

ND means "not done"

The levels of protection seen with killed whole cells are superior to those reported by Nelson et al. [supra] who showed that immunisation with LPS or capsule provided 60% or 20% respectively survival at 21 days post infection.

The results indicate synergy between the protective responses induced by LPS and/or capsular polysaccharide and/or proteins. Preferably all three are present for best protection, but combinations of any two, for instance, LPS and capsule, or LPS and protein provide enhanced protection over say LPS alone.

The findings also have important implications for the understanding of susceptibility to infection in human populations in areas of the world where melioidosis is endemic. It is known that apparently uninfected individuals in these areas develop antibody responses which cross-react with *B. pseudomallei*. The responses noted here appears to provide protection against disease.

EXAMPLE 5

Use of Immunogenic Reagents in Conjunction with Dendritic Cells
Methods
Experimental Animals

BALB/c mice were obtained from Charles River Ltd and maintained under SPF conditions with free access to food and water. All procedures were carried out in accordance with the requirements of the Animals (Scientific Procedures) Act 1986.

Growth of *B. pseudomallei* and heat inactivation of bacteria *B. pseudomallei* K96243-[Holden, M. T. G., et al. *Proceedings of the National Academy of Sciences of the United States of America* 2004, 101(39), 14240-14245] was grown in Luria broth for 18 h at 37° C. in a shaking incubator. A viable count was obtained by culturing aliquots of the broth culture at 37° C. overnight on L-agar plates.

For heat killing of bacteria, broth cultures were harvested by centrifugation and washed three times in PBS, before re-suspending in one-tenth the original volume of PBS. The bacterial cell suspension was then incubated in a water bath at 70° C. for 3 hours, with occasional shaking. After inactivation the suspension was checked for viability by inoculating 10 mL volumes of L-broth with 0.5 mL aliquots of the suspension and incubating at 37° C. for seven days. L-agar plates were then inoculated with the total volume of the broth cultures to check for bacterial growth and incubated for a further seven days. If no growth occurred on the agar plates the bacterial suspension was considered inactivated.

Isolation and culture of dendritic cells from murine bone marrow Procedures were modified and developed from published techniques to optimise the yield and viability of DC's from murine bone marrow. Briefly, bone marrow was extracted from murine rear tibiae and fibulae and cultured at a concentration of $2\times10^6$ cells $mL^{-1}$ in media comprised of RPMI-1640 (Sigma, UK) supplemented with 10% heat inactivated foetal bovine serum (Sigma, UK), 1% penicillin/streptomycin/glutamine (Sigma, UK) and 50 μM 2-mercaptoethanol. The culture medium was supplemented with 20 ng $mL^{-1}$ granulocyte-macrophage colony-stimulating factor, GM-CSF (R&D Systems, Europe) and 10 ng $mL^{-1}$ tumour necrosis factor-alpha, TNF-α (R&D Systems, Europe). Cells were cultured for 96 hours at 37° C. in the presence of 5% $CO_2$ in a fully humidified atmosphere, after which time they were removed from the culture plates by gentle scraping. After washing the cell suspension was layered onto 13.7% metrizamide (w/v; Sigma, UK) and the DC purified using centrifugation.

Immunisation

DC were cultured in the presence of GM-CSF and TNF-α as described. Once isolated and purified from culture, DC were re-suspended to $2\times10^6$ cells $mL^{-1}$ and pulsed with heat killed *B. pseudomallei* K96243 at $10^4$ cfu $mL^{-1}$ for 18-hours at 37° C. in a humidified 5% $CO_2$ environment. CpG 1826 (Coley Pharmaceuticals, Wellesley Mass., USA) was added to some DC cultures at a concentration of 6 μg $mL^{-1}$ when the cells were pulsed with antigen. The cells were then washed three times to remove any extracellular antigen and re-suspended in sterile PBS to a concentration of $1\times10^6$ cells per 100 μL for immunisation by the intradermal (i.d.) route on day 0 and day 21 of the immunisation schedule. When used as an adjuvant concurrently with DC immunisation CpG 1826 was delivered at a dose of 75 μg per mouse in sterile PBS by the intra-venous route.

Primary Response of Naïve Splenocytes

DC were cultured as described, and after washing adjusted to a concentration of $2\times10^6$ cells $mL^{-1}$ in culture media containing 20 ng $mL^{-1}$ GM-CSF and 10 ng $mL^{-1}$ TNF-α. The cells were then incubated with heat killed *B. pseudomallei* ($10^4$ cfu $mL^{-1}$) at 37° C. in a fully humidified environment in 5% $CO_2$ for 18 hours.

Spleens were isolated from naïve mice humanely killed by cervical dislocation and passed through a 70 μm nylon sieve. Red blood cells were removed using lysing buffer (Sigma), the remaining splenocytes were washed, counted and re-suspended to a concentration of $5\times10^6$ cells $mL^{-1}$.

100 μL aliquots of the splenocyte suspension were then added to 96 well tissue culture plates. Replicates of five wells were used for each of the test groups and controls, with 1 μg $mL^{-1}$ concanavalin A (Sigma, UK) being used as a positive control and culture medium as a negative control.

*B. pseudomallei* pulsed DC were washed three times to remove any extracellular antigen, re-suspended to the required concentration in culture medium and added to the splenocyte containing wells of the assay plates in 100 μL aliquots. The plates were then incubated at 37° C. in 5% $CO_2$ for 96 hours.

Following the incubation period, 37 MBq of $^3$H-thymidine were added to each test well on the proliferation plates and the plates re-incubated for a further 6 hours. Cells were then harvested onto 96-well filter plates (PerkinElmer Life Sciences) using an automated cell harvester and the plates allowed to dry at room temperature overnight. Once dry, 20 μl of scintillation fluid (PerkinElmer Life Sciences) was added to each well and the plate sealed before being read on a scintillation counter (PerkinElmer Life Sciences).

Recall Response of Primed Splenocytes

Spleens from mice immunised with heat killed *B. pseudomallei* K96243 pulsed DC were used to assess T cell recall responses to soluble *B. pseudomallei* K96243, NCTC 4845 or strain 576. Spleen cells, ($5\times10_6$ $mL^{-1}$ in 100 μl aliquots) from immunised mice were incubated with heat killed *B. pseudomallei* which was added to the splenocyte cultures in 100 μL aliquots at a concentration of $10_4$ cfu $mL^{-1}$. The cultures were incubated for 72-hours in 5% $CO_2$ at 37° C. before addition of $^3$H-thymidine as described above.

Enzyme Linked Immunosorbant Assay (ELISA) for serum antibody Serum antibody titres to *B. pseudomallei* were assayed by ELISA as previously described [Jones, S. M., et al. *Journal of Medical Microbiology* 2002, 51(12), 1055-1062.], using heat killed *B. pseudomallei* K96243 as the capture antigen. Concentrations of antigen specific IgG were determined using Ascent software (Thermo Labsystems) and the data presented as geometric mean titres with SD.

Elispot Assays for Cytokine Production

Secretion of IL-4 and IFN-γ by spleen cells from naïve and immunised mice was examined by Elispot assay (BD Biosciences ELISPOT kits). On day 35 following the primary immunisation, organs were removed from animals culled by cervical dislocation and forced through disposable 70 μm cell strainers (BD Biosciences) to obtain single cell suspensions. Following centrifugation to pellet the cells, red blood cells were removed using lysing buffer (Sigma). The remaining cells were washed, counted and seeded onto Elispot plates ($4\times10^6$ cells/mL double diluted to $5\times10^5$ cells/mL) in medium containing heat killed *B. pseudomallei* K96243 at a final concentration of $1\times10^4$ cfu mL$^{-1}$. Four replicates were plated for each of 5 samples per treatment group. Concanavilin A (Sigma) at a final concentration of 4 μg mL$^{-1}$ was used as a positive control. Elispot plates were incubated overnight at 37° C., 5% CO$_2$ in a humidified incubator. Assay development was performed according to the kit manufacturer's instructions. The data are presented as means values with SD.

Challenge with *B. pseudomallei*

The growth of, and challenge with *B. pseudomallei* was performed under ACDP containment level III conditions.

*B. pseudomallei* NCTC 4845, 576 and K96243 were grown in overnight culture as described previously and diluted to give an estimated challenge dose of $10^4$ cfu per mouse. Actual challenge doses were determined by overnight culture of inoculum samples at 37° C. on L-agar plates. Groups of 10 BALB/c mice were challenged by the intraperitoneal (i.p.) route on day 35 following primary immunisation and closely observed for 42 days post challenge at which point any survivors were culled. The challenge survivors were assessed for bacterial load by culture of spleens and blood. Organs were passed through 70 μm nylon sieves into sterile PBS and blood, obtained by cardiac puncture was diluted 1:10 in sterile PBS. Samples were innoculated onto L-agar plates and incubated overnight at 37° C. Plates were then examined for the presence or absence of *B. pseudomallei*.

Statistical Analysis

Statistical analyses were performed using the Student's paired t-test for all in vitro experiments. Analysis of the challenge data was performed using PRISM graph pad survival analysis software, and p-values were calculated using the log rank test for trend.

Results

Proliferation Assays

Primary proliferation assays revealed that ex-vivo antigen pulsed DC were capable of inducing proliferation in naïve mouse spleen cells (FIG. 5). Secondary proliferation assays performed with spleen cells from mice immunised with antigen pulsed DC in combination with CpG 1826 showed a significant increase in proliferation when the CpG was used either as a conditioning agent for the DC culture or as an adjuvant with injected DC. The effect was greatest when *B. pseudomallei* K96243 was used as the challenge antigen, however there was still a significant increase in proliferation relative to the in vivo primed, unstimulated controls when other strains of *B. pseudomallei* were used (FIG. 6), indicating that the dendritic cells had extracted common epitopes from the different strains.

Elispot Assays

Elispot assays for IL-4 and IFN-γ were performed at day 35 following primary immunisation. Spleen cells from animals immunised with DC pulsed with heat killed *B. pseudomallei* K96243 in the presence or absence of CpG ODN or those immunised with DC and CpG as an adjuvant were incubated with heat killed *B. pseudomallei* and the number of cytokine producing cells determined. Spleen cells from animals immunised with DC matured in the presence of CpG 1826 produced significantly ($p<0.05$) more IFN-γ positive cells than the DC matured with antigen alone or those matured with antigen and control (non-CpG) ODN (FIG. 7).

ELISA for Serum Antibody

Analysis of serum from immunised mice for *B. pseudomallei* specific immunoglobulin revealed low titres of antibody (FIG. 8) to *B. pseudomallei* K96243. The animals given DC matured in the presence of CpG and those given CpG as an adjuvant with an immunising dose of DC had significantly higher titres than animals given DC alone ($p<0.01$). The presence of antibody reactive with *B. pseudomallei* strains 576 and 4845 was not assayed in view of the low titres developed to the immunising strain.

Protection Against Challenge and Bacterial Clearance

Animals immunised with DC pulsed with *B. pseudomallei* K96243 either with or without CpG treatment were challenged at day 35 following primary immunisation, together with animals given antigen pulsed DC with CpG 1826 co-injected as an adjuvant. The exact challenge doses were determined as; $3.8\times10^4$ cfu for strain K96243, $5.1\times10^4$ cfu for strain 576 and $4.3\times10^4$ cfu for strain 4845.

The animals immunised with DC matured in the presence of CpG 1826 showed the highest levels of protection against all 3 challenge strains of the organism. The use of the CpG ODN as an adjuvant with the DC immunisation also resulted in high levels of protection (60-70%). The control CpG treated DC and DC alone groups showed very poor levels of protection, with no better than 3 of 8 eight mice surviving in the K96243 challenged group (Table 2).

TABLE 2

| Treatment group | Challenge strain/survivors | | |
|---|---|---|---|
| | K96243 | NTCC 4845 | Strain 576 |
| DC + CpG in culture | 9/10 | 7/10 | 7/10 |
| DC + CpG adjuvant | 7/10 | 6/10 | 6/10 |
| Control ODN | 3/8 | 2/8 | 3/8 |
| DC only | 2/10 | 1/10 | 2/10 |
| Naïve | 0/8 | 0/8 | 0/8 |

Challenge survival following intra-dermal immunisation with DC pulsed with heat killed *B. pseudomallei* K96243, with or without CpG ODN treatment. Challenge was with approximately $10^4$ cfu strain K96243, 4845 or 576 by the intra-peritoneal route and survival at day 42 is recorded above.

These results demonstrate that DC immunisation is capable of inducing protective responses in immunised animals, but the addition of CpG ODN greatly increases the levels of protection achievable.

At the end of the post challenge observation period (42 days) splenocytes and blood derived from challenge survivors were cultured at 37° C. for 48 hrs on L-agar (100 μl aliquots in duplicate for each sample). No bacterial growth was detected in any of the samples, indicating that bacterial clearance had been achieved in challenge survivors.

The invention claimed is:

1. An immunogenic agent which is a combination of *Burkholderia pseudomallei* components, which comprises (i) a lipopolysaccharide of *Burkholderia pseudomallei*, (ii) a capsular polysaccharide of *Burkholderia pseudomallei* and (iii) an isolated immunogenic protein of *Burkholderia pseudomallei* or an expression vector incorporating a nucleic acid expressing the immunogenic protein.

2. A composition consisting essentially of (i) a lipopolysaccharide of *Burkholderia pseudomallei*, (ii) a capsular polysaccharide of *Burkholderia pseudomallei* and (iii) an isolated immunogenic protein of *Burkholderia pseudomallei* or an expression vector incorporating a nucleic acid encoding the immunogenic protein.

3. The immunogenic agent of claim 1, wherein component (i) comprises an OPSI and an OPSII *B. pseudomallei* lipopolysaccharide.

4. The immunogenic agent of claim 1, wherein component (iii) comprises one or more isolated immunogenic proteins of *Burkholderia pseudomallei*.

5. The immunogenic agent of claim 1, wherein the isolated immunogenic protein of component (iii) is an isolated surface protein of *B. pseudomallei*.

6. An immunogenic composition comprising the immunogenic reagent of claim 1, in combination with a pharmaceutically acceptable carrier.

7. The immunogenic composition of claim 6, further comprising an adjuvant.

8. The immunogenic composition of claim 7, wherein the adjuvant is a moiety which activates antigen-presenting cells.

9. The immunogenic composition of claim 8, wherein the moiety is one which activates dendritic cells.

10. The immunogenic composition of claim 9, wherein the said moiety is a Toll-like receptor ligand.

11. The immunogenic composition of claim 8, wherein said moiety is a CpG oligonucleotide.

12. A composition comprising the immunogenic agent of claim 1 and antigen-presenting cells.

13. The composition of claim 12, wherein the antigen-presenting cells are dendritic cells.

14. The composition of claim 12, further comprising an adjuvant capable of stimulating antigen-presenting cells.

15. The composition of claim 14, wherein the adjuvant is a CpG oligonucleotide.

16. A method of inducing an immune response to *Burkholderia pseudomallei* and/or *Burkholderia mallei* in an animal, comprising administering to the animal the immunogenic agent of claim 1.

17. A method of inducing an immune response to *Burkholderia pseudomallei* or *Burkholderia mallei* in an animal, comprising administering to the animal the composition of claim 2.

* * * * *